United States Patent [19]
DeLeon et al.

[11] Patent Number: 5,360,900
[45] Date of Patent: Nov. 1, 1994

[54] AROMATIC POLYESTER POLYOL

[75] Inventors: Alberto DeLeon, Kingwood; David J. Shieh, Sugar Land, both of Tex.

[73] Assignee: Oxid, Inc., Houston, Tex.

[21] Appl. No.: 106,127

[22] Filed: Aug. 12, 1993

[51] Int. Cl.$^5$ .................. C07H 15/00; C07H 15/08
[52] U.S. Cl. .................. 536/18.3; 521/172; 521/173; 521/175; 560/88; 560/91; 536/18.5; 536/18.6
[58] Field of Search ............. 536/18.3, 18.6, 18.5; 560/88, 91; 521/172, 173, 175

[56] References Cited

U.S. PATENT DOCUMENTS

| | | | |
|---|---|---|---|
| 3,503,904 | 3/1970 | Dietz et al. | |
| 3,928,253 | 12/1975 | Thornton et al. | |
| 4,469,824 | 9/1984 | Grigsby et al. | 521/173 |
| 4,604,410 | 8/1986 | Altenberg | 521/172 |
| 4,642,319 | 2/1987 | McDaniel | 521/175 |
| 4,644,019 | 2/1987 | McDaniel | 521/173 |
| 4,701,477 | 10/1987 | Altenberg et al. | 521/167 |
| 4,760,100 | 7/1988 | McDaniel | 521/137 |
| 4,789,689 | 12/1988 | Zimmerman et al. | 521/115 |
| 4,902,816 | 2/1990 | McDaniel | 560/88 |
| 4,956,394 | 9/1990 | Kifer et al. | 521/84.1 |
| 4,986,930 | 1/1991 | Lund et al. | 252/182.24 |

FOREIGN PATENT DOCUMENTS

92/00947 1/1992 WIPO .

*Primary Examiner*—John Kight, III
*Assistant Examiner*—Shelley A. Dodson
*Attorney, Agent, or Firm*—Arnold, White & Durkee

[57] ABSTRACT

Two methods for preparing polyester-polyether polyols from polyalkylene terephthalates are disclosed. The first method comprises reacting the polyalkylene terephthalate with a solution of low molecular weight polyols and ethoxylated methyl glucoside at a suitable temperature, generally between about 370° and 450° F., and under vacuum distillation.

The second method comprises dissolving the polyalkylene terephthalates in a mixture of low molecular weight polyols at a suitable temperature and under vacuum distillation to form the polyester polyol component. The polyether polyol component is made by reacting ethoxylated methyl glucoside with an alkylene oxide in the presence of a suitable catalyst. The final product is made by blending about 80-95% by weight of the polyester component with about 5-20% by weight of the polyether component.

23 Claims, No Drawings

AROMATIC POLYESTER POLYOL

BACKGROUND OF THE INVENTION

1. Field of the Invention

This invention relates to the production of polyols that are useful in the preparation of rigid polyurethane and polyisocyanurate foams. More particularly this invention relates to aromatic polyester polyols made from reacting recycled polyethylene terephthalate with a solution of low molecular weight polyols and ethoxylated methyl glucoside.

2. Description of the Related Art

Rigid polyurethane or polyisocyanurate foams generally have good insulating properties and are thus desirable for use in building insulation. As with all building materials, it is desirable to provide rigid foams that are as fire resistant as possible. One approach to this goal is to modify the polyol.

Polyisocyanurate foams are generally fire resistant and show low smoke evolution on burning. However, polyisocyanurate foams tend to be brittle or friable. While various types of polyols have been devised as additives to lower the foam friability, frequently the fire and smoke properties of the polyisocyanurate foam deteriorate. Thus, a fine balance exists between the amount and type of polyol one reacts with a polyisocyanurate foam formulation in order to maintain maximum flame and smoke resistance while at the same time improve foam friability.

Scrap polyalkylene terephthalate, such as polyethylene terephthalate (PET) has been used to advantage by incorporation into polyurethane and polyisocyanurate foams. U.S. Pat. No. 4,604,410 discloses a method for making rigid polyurethane and polyisocyanurate foams which entails reacting an excess of an organic polyisocyanate with an etherified modified aromatic polyol. The etherified modified aromatic polyol is prepared by digesting scrap polyalkylene terephthalate polymers with a low molecular weight polyol, such as diethylene glycol. The resulting product is then blended with a low molecular weight polyol, such as alpha methyl glucoside. The intermediate product is etherified with propylene oxide and/or ethylene oxide.

U.S. Pat. No. 4,701,477 discloses a method for preparing polyester-polyether polyols from polyalkylene terephthalates. This method entails reacting a polyalkylene terephthalate with a low molecular weight polyol, such as diethylene glycol. The reaction product is then blended with an aliphatic polyol such as methyl glucoside. The resulting product is then reacted with an alkylene oxide such as ethylene oxide or propylene oxide to prevent solidification of the methyl glucoside, PET reaction product.

U.S. Pat. No. 4,469,824 teaches a method for making liquid terephthalic esters that are useful as polyol extenders in rigid polyurethane foams and as the sole polyol component in polyisocyanurate foams. The terephthalic esters are made to remain in a liquid form by reacting recycled or scrap polyethylene terephthalate with diethylene glycol and one or more oxyalkylene glycols. Ethylene glycol is then stripped from the reaction to yield a mixture of esters which is free from solids upon standing. Due to solubility limits, a maximum of 5% alpha-methyl glucoside may be added to increase the functionality of the resulting product.

U.S. Pat. No. 4,644,019 discloses a method for preparing an isocyanurate foam that is similar to the methods disclosed above but this method includes reacting an ethoxylate of an alkylphenol, preferably nonylphenol, with the polyethylene terephthalate while it is being digested. The addition of ethoxylated alkyl phenols enhances the solubility of hydrocarbonfluorocarbons, such as Freon 11, in subsequent foam formulations.

Both the fire resistance and the insulation value of polyurethane and polyisocyanurate foams can be increased by expanding the foams with hydrocarbonfluorocarbons (HCFCS). However, the use of HCFCS renders the foams soft, with poor dimensional stability when exposed to cold temperatures. Practitioners have tried to overcome these drawbacks by increasing the functionality of the foams. However, when high functionality and high aromatic content are combined the usefulness of the resulting polyols is lost because their viscosity increases beyond the capabilities of the equipment commonly used for manufacturing the foams.

The novel polyol of this invention solves the aforementioned problems. By combining ethoxylated methyl glucoside or propoxylated methyl glucoside with a polyethylene terephthalate base polyester a polyol is formed which exhibits both high functionality and a high aromatic content at a conventional viscosity.

SUMMARY OF THE INVENTION

A method is disclosed describing how to prepare polyester-polyether polyols from polyalkylene terephthalates. This method entails reacting a polyethylene terephthalate with a solution of low molecular weight polyols and ethoxylated methyl glucoside or propoxylated methyl glucoside at a suitable temperature effective for transesterification reactions and under vacuum distillation. The low molecular weight polyols preferably include a mixture of polyols comprising diethylene glycol, triethylene glycol and tetraethylene glycol. The ethoxylated methyl glucoside includes a mixture of ethoxylated alpha methyl glucoside and ethoxylated beta methyl glucoside. The ethoxylated alpha methyl glucoside and ethoxylated beta methyl glucoside are preferably combined in a 1:1 ratio.

A second method is disclosed for preparing polyester-polyether polyols from polyalkylene terephthalates. The first step of this method entails dissolving polyalkylene terephthalates in a mixture of low molecular weight polyols at a suitable temperature effective for transesterification reactions and under vacuum distillation to form the polyester polyol component. The polyether polyol is made by reacting ethoxylated methyl glucoside or propoxylated methyl glucoside with an alkylene oxide in the presence of a suitable catalyst. The finished polyol is made by blending the polyester polyol component and the polyether polyol component. Approximately 80–95% by weight of the polyester polyol is blended with approximately 5–20% by weight of the polyether polyol.

The methods of the invention provide novel polyester-polyether polyols having high functionality (2.3–3.0), high aromatic content (34–42%), and a conventional viscosity (ranging between 3,000 to 25,000 CPS at 25° C). These polyester-polyether polyols are especially useful for making polyurethane and polyisocyanurate foams with improved thermal stability and insulation values.

DESCRIPTION OF THE PREFERRED EMBODIMENTS

The polyalkylene terephthalate polymers which are the source of the aromatic polyols of the present invention can be obtained from a variety of waste materials, such as used photographic films, X-ray films, and the like; synthetic fibers and waste materials generated during their manufacture; used plastic bottles and containers such as the soft plastic beverage containers now widely used by the soft drink industry; and waste materials from the production of other products made from polyalkylene terephthalate polymers.

Polyalkylene terephthalate polymers which are suitable for the present invention will generally have the formula:

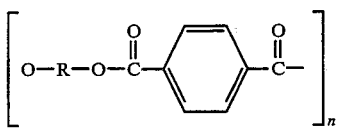

wherein R is a divalent aliphatic radical having from two to ten carbon atoms and attached to the adjacent oxygen atoms by saturated carbon atoms. Most frequently, R is an ethylene radical to form polyethylene terephthalate or will be a butylene radical to form polybutylene terephthalate. The number of recurring units n will generally be at least 75, frequently being 500 or greater, and the molecular weight will be greater than 15,000 daltons, usually being greater than 100,000 daltons.

The low molecular weight solvent used for digesting the polyethylene terephthalate polymers is a polyol. Suitable polyols are typically diols or triols. Suitable diols include ethylene glycol, propylene glycol, butylene glycol, diethylene glycol, polyethylene glycol triethylene glycol, dipropylene glycol, butylene glycol, polyethylene glycol, and mixtures thereof. Suitable triols include glycerine, triethanolamine, trimethylol propane, trimethylol ethane, alkoxylated products of these and mixtures thereof.

The low molecular weight polyols preferably include a mixture of polyols comprising diethylene glycol, triethylene glycol and tetraethylene glycol. A small amount of a polyfunctional alcohol such as pentaerythritol may also be included.

The ethoxylated methyl glucoside includes a mixture of ethoxylated alpha methyl glucoside and ethoxylated beta methyl glucoside. The ethoxylated alpha methyl glucoside and ethoxylated beta methyl glucoside are combined in a 0.1:1.0 to 1.0:0.1 ratio, preferably in a 1:1 ratio. A mixture of propoxylated alpha methyl glucoside and propoxylated beta methyl glucoside can also be used.

Halogen-containing anhydrides, such as tetrachlorophthalic anhydrides, may be utilized to produce a halogen-containing digestion product. Such halogen-containing polyols are particularly desirable for manufacturing flame retardant polyurethane foams.

As stated above, the process of the present invention will normally be carried out with waste or scrap polyalkylene terephthalate polymers, typically polyethylene terephthalate polymers in the form of used photographic film, used soda bottles, and the like. When using such recycled materials, it is necessary to first clean the materials to remove dirt, oil, debris, labels, and the like.

In the case of photographic films, it is necessary to remove the emulsion layer and substratum from the film prior to digestion. The emulsion layer can be removed by washing with hot water, while the substratum is typically removed with an alkylene glycol or monoethanolamine wash.

Useful methods for preparing spent photographic films are described in U.S. Pat. Nos. 3,503,904 to Dietz et. al., and 3,928,253 to Thornton et. al., the disclosures of which are incorporated herein by reference. After cleaning, the polyalkylene terephthalate polymers will be cut into small pieces, typically having dimensions from $\frac{1}{4}$ to $\frac{1}{2}$ inch.

The polyester polyol of the instant invention may be made by either of two methods. The first method involves reacting all the components together. This method entails dissolving polyalkylene terephthalate in a mixture of glycols and ethoxylated methyl glucoside. The polyalkylene terephthalate and polyol are normally added at a 1:1.4 molar ratio; however, molar ratios of 0.5:1.0 to 1.0:0.5 polyalkylene terephthalate:polyol can be used with satisfactory results. The ethoxylated or propoxylated methyl glucoside is added preferably at a 1:.15 molar ratio of polyalkylene terephthalate:glucoside, and suitably from 1:.05 to 1:0.4. A transesterification reaction is then carded out suitably at a temperature of 390°–430° F. under vacuum conditions, with or without a suitable catalyst. The reaction is carried out so that at least 50% of the ethylene glycol that is liberated from the transesterification is removed from the mixture by vacuum distillation. The ethylene glycol is derived from the PET during the reaction and contributes to solid precipitation when the mixture is left standing. The amount of ethoxylated or propoxylated methyl glucoside present in the resulting polyol should be between 5–25% by weight of the resulting composition.

The second method that may be used to prepare the polyols of the instant invention involves blending the two components. The polyester polyol component is made by dissolving polyalkylene terephthalate in a glycol mixture. A small amount (1 to 5 wt %) of a polyfunctional alcohol such as pentaerythritol can also be present in the glycol mixture to prevent crystallinity. A transesterification reaction is then carried out suitably at a temperature between about 370°–450° F. and preferably between about 390°–430° F. under vacuum conditions. Ethylene glycol is removed from the reaction mixture by vacuum distillation. Removal of the ethylene glycol prevents the polyalkylene terephthalate from precipitating in the reaction mixture. The transesterification catalyst need not be present.

The polyether polyol component is made by reacting one mole of ethoxylated methyl glucoside with 4–5 moles of ethylene oxide in the presence of a suitable catalyst. Potassium hydroxide, tertiary amine and anhydrous ammonia are examples of suitable catalysts. The preferred polyether polyol of this invention is prepared by reacting a 1:1 blend of an ethoxylated alpha: ethoxylated beta methyl glucoside in an aqueous solution with 4–5 moles of ethylene oxide. The amount of water present in the reaction mixture should not exceed 1 mole. In the initial stage of the reaction, the water is reduced to approximately 10%, and about one fourth of the ethylene oxide required is charged into the reaction mixture. Upon completion of this reaction, the remaining water is removed until the mixture contains about 0.25% water by weight. At this point the remaining ethylene oxide is added. The resulting polyether polyol component should exhibit a hydroxyl number between 500 and 650 and a viscosity between 1500 and 100,000 CPS at 25° C.

The finished polyol is made by blending the polyester polyol component with the polyether polyol component. The components are combined in the following ratios. The polyester polyol will constitute approximately 80–95% of the resulting product and the polyether polyol will constitute approximately 20–5% of the resulting product. Preferably, the polyester polyol component will comprise approximately 80–90 % of the resulting product and the polyether polyol will constitute approximately 20–10% of the resulting product.

Regardless of the procedure that is used to prepare the instant polyols the finished polyol should exhibit the following characteristics:

| | |
|---|---|
| Hydroxyl Number: | 250–400 |
| Viscosity: | 3000–25,000 CPS at 25° C. |
| Percent Terephthaloyl: | 25–45% w/w |
| Percent Ethylene Glycol: | 0–5% w/w |
| Percent Diethylene Glycol: | 10–30% w/w |
| Percent Triethylene Glycol: | 5–30% w/w |
| Percent Tetraethylene Glycol: | 2–20% w/w |
| Percent Pentaerythritol: | 0–5% w/w |
| Percent Polyether: | 5–25% w/w |

The polyester-polyether polyols of this invention are employed to produce polyurethane and polyisocyanurate foams in the conventional manner. The polyol is reacted with a suitable amount of polyisocyanurate in the presence of an appropriate blowing agent, catalyst, surfactant, fire retardants, fillers, etc. U.S. Pat. Nos. 4,644,019, 4,604,410 and 4,469,824 (incorporated by reference herein), for example, expound in detail on the various ingredients and conventional methods of producing polyol foams.

EXAMPLE 1

To a 5,000 ml resin kettle fitted with a mechanical stirrer, a thermometer, a reflux condenser and a heating mantel, we added 1249 grams of diethylene glycol, 1669 grams of recycled polyethyleneterephthalate and 3 grams of Tyzor ® TE. Tyzor ® TE is a triethanolamine titanate thelate sold by DuPont.

The reaction mixture was heated to 430° F. with constant agitation; held at 430° F. for two hours then cooled to 350° F. The material was transferred to a five liter flask fitted with a perforated plate distilling column and 360 grams of ethoxylated alpha, beta methyl glycoside in a 1:1 ratio (obtained from Ele Corp. of Lyons, Ill.) was added before proceeding to the next step.

The reaction mixture was heated to 430° F. under 100 mm mercury vacuum. Total reflux occurred at around 370° F. Ethylene glycol was removed from the reaction mixture by condensing the overhead through a divider with a reflux overhead ratio of 3:1.

When the total overhead reached 330 grams, the reaction was stopped. The yield of reaction was 89.93 %. The finished polyol was in the form of a clear, viscous liquid with a hydroxyl number of 294, viscosity at 77° F. of 29,400 cps, and acid value of less than one. After three months at room temperature, the polyol was clear and stable.

EXAMPLE 2

To a 5,000 ml resin kettle fitted with a mechanical stirrer, a thermometer, a reflux condenser and a heating mantel, we added 815.5 grams of diethylene glycol, 469.2 grams of triethylene glycol, 1485 grams of recycled polyethyleneterephthalate and 3 grams of Tyzor ® TE.

The reaction mixture was heated to 430° F. with constant agitation; held at 430° F. for two hours then cooled to 350° F. The material was transferred to a five liter flask fitted with a perforated plate distilling column and 427.7 grams of ethoxylated alpha, beta methyl glycoside in a 1:1 ratio was added before proceeding to the next step.

The reaction mixture was heated to 430° F. under 100 mm mercury vacuum. Total reflux occurred at around 370° F. Ethylene glycol was removed from the reaction mixture by condensing the overhead through a divider with a reflux/overhead ratio of 3:1.

When the total overhead reached 230 grams, the reaction was stopped. The yield of reaction was 92.81%. The finished polyol was in the form of a clear, viscous liquid with a hydroxyl number of 301, viscosity at 77° F. of 12,160 cps, and acid value of less than one. After three months at room temperature, the polyol was clear and stable.

EXAMPLE 3

To a 5,000 ml resin kettle filled with a mechanical stirrer, a thermometer, a reflux condenser and a heating mantel, we added 474 grams of diethylene glycol, 804.3 grams of triethylene glycol, 495.6 grams of tetraethylene glycol, 1830 grams of recycled polyethyleneterephthalate and 3 grams of Tyzor ® TE.

The reaction mixture was heated to 430° F. with constant agitation; held at 430° F. for two hours then cooled to 350° F. The material was transferred to a five liter flask fitted with a perforated plate distilling column and 192.2 grams of ethoxylated alpha, beta methyl glycoside in a 1:1 ratio was added before proceeding to the next step.

The reaction mixture was heated to 430° F. under 100 mm mercury vacuum. Total reflux occurred at around 370° F. Ethylene glycol was removed from the reaction mixture by condensing the overhead through a divider with a reflux/overhead ratio of 3:1.

When the total overhead reached 295 grams, the reaction was stopped. The yield of reaction was 92.23 %. The finished polyol was in the form of a clear, viscous liquid with hydroxyl number of 272, viscosity at 77° F. of 7,680 cps, and acid value of less than one. After three months at room temperature, the polyol was clear and stable.

EXAMPLE 4

PREPARATION OF ETHOXYLATED METHYL GLUCOSIDE

To a 2,000 ml autoclave fitted with a mechanical stirrer, a thermometer, a nitrogen inlet and outlet, oxide dip tube heating jacket and water cooling coil, we added 800 grams of EM201 (80% water solution of alpha/beta methyl glucoside 1:1). The reactor was heated to 250° F. and the water constant of EM201 reduced from 20% to 10% with the aid of nitrogen sparging or vacuum. The pH value of EM201 was adjusted by adding 85% potassium hydroxide until the pH was greater than 8.

The contents of the autoclave were heated to 250° F. At this point, 213 grams of ethylene oxide was added very slowly. Once the pressure in the autoclave returned to safe levels, the moisture content of the mixture was reduced to 0.5%.

To this mixture, 431 grams of ethylene oxide was added. The temperature was increased to 300° F. and held for two hours after all of the ethylene oxide was added. Ethylene oxide was removed by nitrogen sparging.

A dark, clear, stable liquid resin was generated with hydroxyl number of 650, viscosity of 15,000 cps at 77° F.

Ethylene oxide is added in two steps. First, some is added after reducing water from 20% to 10%. Then water is removed completely and ethylene oxide is added again. This method minimizes the formation of glycol.

Example 4 shows how to make the ethoxylated methyl glucoside that is used in all the examples of the invention that show how to make the polyester.

EXAMPLE 5 (COMPARATIVE)

To a 3,000 ml resin kettle fitted with a mechanical stirrer, a thermometer, a reflux condenser and a heating mantel, we added 788 grams of diethylene glycol, 147 grams of triethylene glycol, 95 grams of tetraethylene glycol, 985.8 grams of recycled polyethyleneterephthalate and 2 grams of Tyzor ® TE.

The reaction mixture was heated to 430° F. with constant agitation; held at 430° F. for two hours then cooled to 350° F. The material was transferred to a five liter flask fitted with a perforated plate distilling column and 195.6 grams of ethoxylated alpha methyl glycoside (99% pure) was added before proceeding to the next step.

The reaction mixture was heated to 430° F. under 100 mm mercury vacuum. Total reflux occurred at around 370° F. Ethylene glycol was removed from the reaction mixture by condensing the overhead through a divider with a reflux/overhead ratio of 3:1.

When the total overhead reached 210.7 grams, the reaction was stopped. The yield of reaction was 90.47%. The finished polyol was black viscous liquid with hydroxyl number of 349, viscosity at 77° F. of 7,000 cps, and acid value of less than one.

After standing for one week, the polyol was hazy. A 2-3% precipitate, (by volume) was observed.

EXAMPLE 6 (COMPARATIVE)

To a 3,000 ml resin kettle fitted with a mechanical stirrer, a thermometer, a reflux condenser and a heating mantel, we added 788 grams of diethylene glycol, 147 grams of triethylene glycol, 95 grams of tetraethylene glycol, 985.6 grams of recycled PET and 195.6 grams of solid alpha methyl glucoside (99.9% pure) and 2 grams of Tyzor ® TE.

The reaction mixture was heated to 430° F. with constant agitation; held at 430° F. for four hours then cooled down to room temperature.

The yield of reaction was 100%. The finished polyol was a black, dark, soft solid with hydroxyl number of 521 and acid value of less than one.

The dark color indicates that alpha methyl glycoside decomposed in the reaction mixture at high temperature.

EXAMPLE 7

The following foams were made using the polyester-polyether polyols described in the above examples.

| SPRAY FOAM FORMULA | | EQWT | WT |
|---|---|---|---|
| Polyol | TR385 | 155.83 | 30.00 |
| Polyether 2 | R470X | 120.00 | 60.00 |
| Sufactant | DC193 | | 2.00 |
| CAT 1 | PC8 | | 1.20 |
| CAT 2 | PB NAPH | | 0.30 |
| Water | | 9.00 | 0.50 |
| R141B | | | 22.00 |
| TOTAL | | | 126.00 |
| Index | | | 1.05 |
| ISO Total | | 134.00 | 105.25 |
| A + B | | | 231.25 |
| % R141 | | | 9.513 |
| A/B | | | 0.84 |
| B/A | | | 1.197 |
| A & B @ 70 F., Mixed 10 Seconds Reactivity (seconds) | | | |
| Cream | | | 2 sec |
| Gel | | | 10 sec |
| Tack Free | | | 13 sec |
| Core Dens. lbs/ft | | | 2.50 |
| Comprehensive Strength | | | 45 PSI |

| CLASS I PANEL FORMULATION | | | |
|---|---|---|---|
| | | EQWT | WT |
| FORMULA | | | |
| Polyol | TR375 | 165.00 | 30.00 |
| Polyether 1 | R575 | 97.57 | 33.00 |
| Polyether 2 | PHT4 DIOL | 260.00 | 27.00 |
| Additive | PCF | | 5 |
| Surfactant | B8408 | | 1.50 |
| CAT 1 | PC8 | | 1.20 |
| CAT 2 | DABCO33LV | | 0.85 |
| Water | | 9.00 | 0.50 |
| R141B | | | 25.88 |
| TOTAL | | | 124.93 |
| % Aromatic | | | 4.44 |
| % Sucrose | | | 14.37 |
| Index | | | 1.15 |
| ISO TOTAL | RUBM | 134.00 | 104.70 |
| B/A | | | 1.193 |
| A + B | | | 229.63 |
| % R141B | | | 11.270 |
| % Bromine | | | 5.53 |
| Reactivity, secs | | | |
| Cream | | | 11.00 |
| Gel | | | 25.00 |
| Tack Free | | | 33.00 |
| FOAM PROPERTIES | | | |
| Core Density lbs/ft$^3$ | | | 1.66 |
| Comprehensive Strength | | | 25 PSI |
| Dimensional Stability | | | |
| % Volume Growth | | | |
| 70C/95% RH | | | 12.00 |
| 200 F. | | | 10.0 |
| K-Factor | | | 0.125 |
| Flame Spread | | | 25 |
| Smoke | | | 250 |

| REFRIGERATION FOAM FORMULA | | EQWT | WT |
|---|---|---|---|
| Polyol | TR375 | 155.83 | 30.00 |
| Polyether 1 | M9166 | 144.00 | 10.00 |
| Polyether 2 | R575 | 97.57 | 60.00 |
| Surfactant | DC193 | | 2.00 |
| CAT 1 | PC5 | | |
| CAT 2 | PC8 | | 1.10 |
| Water | | 9.00 | 1.00 |
| R141B | | | 38.19 |
| TOTAL | | | 142.68 |

| REFRIGERATION FOAM | | |
|---|---|---|
| FORMULA | EQWT | WT |
| Index | | 1.05 |
| ISO TOTAL | 134.00 | 139.02 |
| A + B | | 281.70 |
| % R141 | | 13.557 |
| A/B | | 0.97 |
| B/A | | 1.026 |
| A % B @ 70 F., Mixed 10 Seconds Reactivity (secs) | | |
| Cream | | 21 |
| Gel | | 63 |
| Tack Free | | 92 |
| Core Dens., lb/ft$^3$ | | 1.42 |

| GLOSSARY |
|---|
| TR375, Polyol of this invention Example 8 & 9, OXID |
| TR385, Polyol of this invention Example 7, OXID |
| M9166, Aromatic amino polyol |
| R575, Sucrose polyol, Eastman |
| R470X, Aromatic amino polyol, Eastman |
| PHT4 DIOL, Tetrabromo phthalic anhydride, propoxylated |
| DC193, Silicone surfactant, Dow Corning |
| B8408, Silicone surfactant, Goldschmidt |
| PC5, Polycat 5, amine catalyst, Airproducts |
| PC8, Polycat 8, amine catalyst, Airproducts |
| DABCO33LV, Amine catalyst, Air Products |
| PBNAPH, Lead naphthanate, Mooney |
| R141B, HCFC blowing agent, Atochem |
| RM, Polymeric isocynate |

The foregoing description has been limited to specific embodiments of the invention. It will be apparent, however, that variations and modifications can be made to the invention, with the attainment of some or all of the advantages of the invention. Therefore it is the object of the appended claims to cover all such variations and modifications as come within the true spirit and scope of the invention.

What is claimed is:

1. A method for preparing polyester-polyether polyols from polyalkylene terephthalates, said method comprising:

reacting the polyalkylene terephthalate in a solution of a low molecular weight polyol and a mixture of alkoxylated alpha and alkoxylated beta methyl glucoside at a temperature in the range of about 370° to about 450° F. and under vacuum distillation.

2. The method of claim 1 wherein said mixture of alkoxylated methyl glucosides comprises either ethoxylated alpha and ethoxylated beta methyl glucoside or propoxylated alpha and propoxylated beta methyl glucoside.

3. The method of claim 1 wherein said alkoxylated alpha methyl glucoside and said alkoxylated beta methyl glucoside are combined in a 0.1:1.0 to 1.0:0.1 ratio.

4. The method of claim 1 wherein said alkoxylated alpha methyl glucoside and said alkoxylated beta methyl glucoside are combined in a 1:1 ratio.

5. The method of claim 1 wherein said low molecular weight polyols are diols or triols.

6. The method of claim 5 wherein said diols are selected from the group consisting of ethylene glycol, diethylene glycol, triethylene glycol, tetraethylene glycol, propylene glycol, dipropylene glycol, butylene glycol, polyethylene glycol and polypropylene glycol and mixtures thereof.

7. The method of claim 5 wherein said triols are selected from the group consisting of glycerine, triethanol-amine, trimethylol propane, trimethylol ethane, their alkoxylated products and mixtures thereof.

8. The method of claim 1 wherein said solution of low molecular weight polyols comprises diethylene glycol, triethylene glycol and tetraethylene glycol.

9. The method of claim 1 wherein said method further comprises the addition of a catalyst.

10. The method of claim 9 wherein said catalyst is a triethanolamine titanam chelate.

11. A method for preparing polyester-polyether polyols from polyalkylene terephthalates said method comprising:

(a) dissolving said polyalkylene terephthalates in a mixture of a low molecular weight polyols at a temperature in the range of about 370° F. to about 450° F. and under vacuum distillation;

(b) reacting a mixture of alkoxylated alpha and alkoxylated beta methyl glucoside with an alkylene oxide in the presence of a suitable catalyst to form a polyether polyol; and (c) blending the product formed in step (a) with the polyether polyol product formed in step (b) in a weight ratio of approximately 80-95% of (a) to approximately 5-20% of (b).

12. The method of claim 11 wherein said mixture of alkoxylated methyl glucosides comprises either ethoxylated alpha and ethoxylated beta methyl glucoside or propoxylated alpha and propoxylated beta methyl glucoside.

13. The method of claim 11 wherein said alkoxylated alpha methyl glucoside and said alkoxylated beta methyl glucoside are combined in a 0.1:1.0 to 1.0:0.1 ratio.

14. The method of claim 11 wherein said alkoxylated alpha methyl glucoside and said alkoxylated beta methyl glucoside are combined in a 1:1 ratio.

15. The method of claim 11 wherein said low molecular weight polyols are diols or triols.

16. The method of claim 15 wherein said diols are selected from the group consisting of ethylene glycol, diethylene glycol, triethylene glycol, tetraethylene glycol, propylene glycol, dipropylene glycol, butylene glycol, polyethylene glycol and polypropylene glycol and mixtures thereof.

17. The method of claim 15 wherein said triols are selected from the group consisting of glycerine, triethanol amine, trimethylol propane, trimethylol ethane, their alkoxylated products and mixtures thereof.

18. The method of claim 11 wherein said solution of low molecular weight polyols comprises diethylene glycol, triethylene glycol and tetraethylene glycol.

19. The method of claim 11 wherein said solution of low molecular weight polyols further comprises a polyfunctional alcohol.

20. The method of claim 19 wherein said polyfunctional alcohol is pentaerythritol.

21. A polyol produced according to the method of any one of claims 1 to 20.

22. The method of claim 11 wherein the alkylene oxide is ethylene oxide.

23. The method of claim 11 wherein the catalyst is potassium hydroxide, tertiary amine or anhydrous ammonia.

* * * * *

UNITED STATES PATENT AND TRADEMARK OFFICE
CERTIFICATE OF CORRECTION

PATENT NO. : 5,360,900
DATED : November 1, 1994
INVENTOR(S) : Alberto DeLeon/David J. Shieh It is certified that error appears in the above-indentified patent and that said Letters Patent is hereby corrected as shown below:

At column 5, line 45, please delete "thelate" and insert therefor --chelate--.

Column 10
In claim 10, line 2, please delete "titanam" and insert therefor --titanate--.

Signed and Sealed this

Twenty-eight Day of February, 1995

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,360,900
DATED : November 1, 1994
INVENTOR(S) : Alberto DeLeon/David J. Shieh It is certified that error appears in the above-indentified patent and that said Letters Patent is hereby corrected as shown below:

Title page, item [57], col. 2,
In the Abstract, line 13, please delete "ethoxylated".

In column 2, line 52, please delete "ethoxylated"; and at line 53, please delete "or propoxylated methyl glucoside".

In column 4, line 54, please delete "ethoxylated".

Column 10,
In claim 11, lines 8-9, please delete "alkoxylated" in both instances.

Column 10,
In claim 12, line 1, please add the word --reacted-- before "mixture".

Column 10,
In claim 13, lines 1-2, please delete "alkoxylated" in both instances.

Column 10,
In claim 14, please delete "alkoxylated" in both instances.

Signed and Sealed this

Twentieth Day of June, 1995

Attest:

BRUCE LEHMAN

*Attesting Officer*         *Commissioner of Patents and Trademarks*